United States Patent [19]

Powell

[11] 4,061,749

[45] Dec. 6, 1977

[54] 5,6-DIHYDRO-4H-1,3-THIAZINE-2-CARBOXALDEHYDE OXIME USEFUL AS INSECTICIDES

[75] Inventor: James E. Powell, Kent, England

[73] Assignee: Shell Oil Company, Houston, Tex.

[21] Appl. No.: 703,043

[22] Filed: July 6, 1976

[51] Int. Cl.$^2$ .................. A01N 9/00; A01N 9/12; C07D 279/00; C07D 285/00

[52] U.S. Cl. ............................. 424/246; 544/53

[58] Field of Search .................. 424/246; 260/243 R

[56] References Cited

U.S. PATENT DOCUMENTS 3,993,648  11/1976  Powell ........................... 260/243 R Primary Examiner—Albert T. Meyers
Assistant Examiner—D. W. Robinson

[57] ABSTRACT

5,6-Dihydro-4H-1,3-thiazine-2-carboxaldehyde oxime useful as an insecticide.

5 Claims, No Drawings

5,6-DIHYDRO-4H-1,3-THIAZINE-2-CARBOXALDEHYDE OXIME USEFUL AS INSECTICIDES

DESCRIPTION OF THE INVENTION

It has been found that useful insecticidal activity is possessed by the oxime of 5,6-dihydro-4H-1,3-thiazine-2-carboxaldehyde, said oxime having the formula:

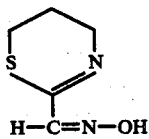

H—C=N—OH

This compound exists in the form of two geometric isomers, the E isomer (hereinafter designated as Compound 1) and the Z isomer, hereinafter designated as Compound 2. This invention contemplates both isomers, as well as mixtures thereof.

The compound of the invention was prepared as follows:

To a mixture of 235 g of 5,6-dihydro-2-methylthio)-4H-1,3-thiazine (A. F. McKay et al., J. Am. Chem. Soc., 80, 3339 (1958)) and 2 g of zinc chloride at approximately 115° in a nitrogen atmosphere, 263 g of ethyl nitroacetate (S. Zen, et al., Kogyo Kagaku Zasshi, 74, 70 (1971)) was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled solution of 2/1 (volume) ether/isopropyl alcohol mixture. The crystallized product was collected, washed with ether and dried under reduced pressure to leave a tan solid, m.p. 100°–102°, which on recrystallization from methanol gave ethyl nitro(tetrahydro-2H-1,3-thiazin-2-ylidene)acetate (1A) as a pale yellow solid, m.p. 105°–106°.

2.3 g of 1A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give tetrahydro-2--(nitromethylene)-2H-1,3-thiazine (1B) as a pale yellow solid, m.p. 76°–78°.

A solution of 4.8 g of 1B in 30 ml of tetrahydrofuran was added dropwise to a suspension of 1.35 g of oil-free sodium hydride in 30 ml of tetrahydrofuran and 10 ml of hexamethylphosphoramide, at 20°–25°. 15 minutes after the addition was complete, a solution of 4.8 g of diethyl sulfate in 20 ml of tetrahydrofuran was added dropwise, at 17°–19°. The resulting mixture then was allowed to warm and stirred at room temperature for 2.5 hours, then at 45°–50° for 5 hours, then at room temperature overnight. The reaction mixture was poured into water and the resulting mixture was extracted with methylene chloride. The extract phase was dried (Na$_2$SO$_4$) and the solvent was evaporated under reduced pressure to give an amber liquid. The liquid was chromatographed (dry column technique) on silica gel, using Solvent No. 3 (a 4/30/66 by volume mixture of tetrahydrofuran; ethyl acetate and hexane) as eluent. This developed two bands, which were cut out and extracted. The more polar band, consisting of two components, gave an amber oil, which was dissolved in a little ethanol; the solution was cooled to give a white solid, m.p.: 55°–58° (1C). On standing over a week-end, crystals separated from the mother liquor. Filtration and washing with cold ethanol gave a small amount of white solid, m.p.: 134°–139° (1D). The filtrate was evaporated and the residue was chromatographed on silica gel (dry column technique), using Solvent No. 3 as eluent, to give two components. The more polar component yielded a white solid (1E), which was recrystallized from ethyl acetate to give the E-isomer of the oxime of 5,6-dihydro-4H-1,3--thiazine-2-carboxaldehyde, i.e., Compound 1, as a white solid, m.p.: 139°–140.5°. The mother liquor from crystallization of 1E was crystallized from a mixture of ethyl acetate and ether to give additional E-isomer, as a white solid, m.p.: 138°–139.5°. Spectral data confirmed the identity of the E-isomer, indicating that 1D also was E-isomer.

The above procedure was repeated and the same amber liquid product was obtained. This was chromatographed on silical gel (dry column technique) using Solvent No. 3 as eluent, to give two products. The less polar was recrystallized from a mixture of hexane and ether to give a light pink solid, which was recrystallized from the same solvent mixture to give the Z-isomer of the oxime of 5,6-dihydro-4H-1,3-thiazine-2--carboxaldehyde, i.e., Compound 2, as a tan solid, m.p.: 54°–57°, its identity being confirmed by appropriate spectral analyses.

Although the product 1C was not identified by spectral analyses, it is to be noted that its melting point is consistent with that of the Z-isomer Compound 2.

Compound 1 also was prepared by the following method:

To a solution of 80.0 g of 1B in 500 ml of methylene chloride was added over 0.5 hour 43 ml of methyl fluorosulfonate. The heat of reaction brought the solution to reflux during the addition. The next day 200 ml of water and 64 g of sodium bicarbonate were added and the mixture was stirred for 20 minutes. The organic phase was separated, dried with magnesium sulfate, diluted with 200 ml of methanol and refluxed for 5 hours, during which time methylene chloride was distilled off to increase the reflux temperature to about 50°. The next day, the mixture was treated with 300 ml of 10% aqueous sodium hydroxide solution and washed with methylene chloride. The base solution was cooled in ice, acidified with 43 ml of acetic acid and extracted with methylene chloride. The extracts were poured on a florisil column and eluted with a 10% solution of ethyl acetate in methylene chloride. The yellow, solid product was recrystallized from acetone to give 1, as a cream colored solid, m.p.: 139°–140°.

Both isomers of the compound of this invention exhibit useful insecticidal activity, being of particular interest for control of the larval "caterpillar" or "worm" forms of lepidopterous insects of the genus Heliothis, such as H. zea (corn earworm, cotton bollworm, tomato fruitworm), H. virescens (tobacco budworm); the genus Agrotis, such as A. ipsilon (black cutworm); the genum Trichoplusia, such as T. ni (cabbage looper), and the genus Spodoptera, such as S. littoralis (Egyptian cotton leafworm).

The activity of the isomers, i.e., Compounds 1 and 2, with respect to insects was determined by using standardized test methods to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted spider mite. Activity with respect to mosquito larvae was determined by placing the larvae in water containing the test compound.

Compounds 1 and 2 were found to be inactive with respect to the mites and slightly active with respect to mosquito larvae. They both were active with respect to the houseflies and pea aphids, and were moderately active with respect to the corn earworms. In the course of the tests it was noted that compound 2 acted very quickly on the houseflies and aphids and that both compounds acted very quickly on the corn earworms.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the salts of this invention and liquids in which the toxicant is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchlorethylene, trichloroethane; including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10%w of active ingredient. Granules may be manufactured by agglomeration or impregnation techniques. Generally, granules will contain ½-25%w active ingredient and 0-10%w of additives such as stabilizers, slow release modifiers and binding agents. Emulsifiable concentrates usually contain, in addition to the solvent, and when necessary, co-solvent, 10-50%w/v active ingredient, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w active ingredient, 0-5%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the effective dosage of salts of this invention at the locus to be protected — i.e. the dosage to which the insect contacts — is of the order of 0.001% to 0.5% based on the total weight of the formulation, though under some circumstances the effective concentration will be as little as 0.001% or as much as 2%, on the same basis.

I claim:

1. The oxime of the formula

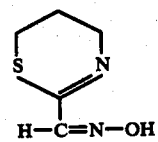

2. The E-isomer of the oxime of claim 1.
3. The Z-isomer of the oxime of claim 1.
4. A method for killing lepidopterous insects which comprises contacting them with an insecticidally effective amount of the oxime of claim 1.
5. An insecticidal composition comprising an insecticidally effective amount of the oxime of claim 1 together with a pesticide carrier and optionally a surface-active agent.

* * * * *